United States Patent

Wentz

Patent Number: 5,095,499
Date of Patent: Mar. 10, 1992

[54] ORIENTED MAMMOGRAPHY PHANTOM

[76] Inventor: Virginia R. Wentz, 310 Waterside Dr., Little Ferry, N.J. 07643

[21] Appl. No.: 417,283

[22] Filed: Oct. 5, 1989

[51] Int. Cl.$^5$ .............................................. A61B 6/04
[52] U.S. Cl. ........................................ 378/37; 378/207
[58] Field of Search ................................... 378/37, 207

[56] References Cited

U.S. PATENT DOCUMENTS

| 4,649,561 | 3/1987 | Arnold | 378/207 |
| 4,669,104 | 5/1987 | Manganet et al. | 378/207 |
| 4,759,045 | 7/1988 | Lasky | 378/207 |

OTHER PUBLICATIONS

Computerized Imaging Reference Systems, Inc., Norfolk, Virginia, "Tissue-Equivalent Breast Phantoms".

Primary Examiner—Craig E. Church
Attorney, Agent, or Firm—Lerner, David, Littenberg, Krumholz & Mentlik

[57] ABSTRACT

A mammographic phantom is disclosed having an orienting feature which permits the consistant placement of the phantom in the imaging plane of an X-ray beam. The phantom includes test objects which indicate the resolution capability of the X-ray system, as well as a step wedge which indicates X-ray beam quality. Consistant orientation permits the image of the test objects to be readily located on an exposed X-ray film and permits the step wedge to be accurately positioned adjacent the center of the X-ray beam to thereby reduce scattering affects.

7 Claims, 2 Drawing Sheets

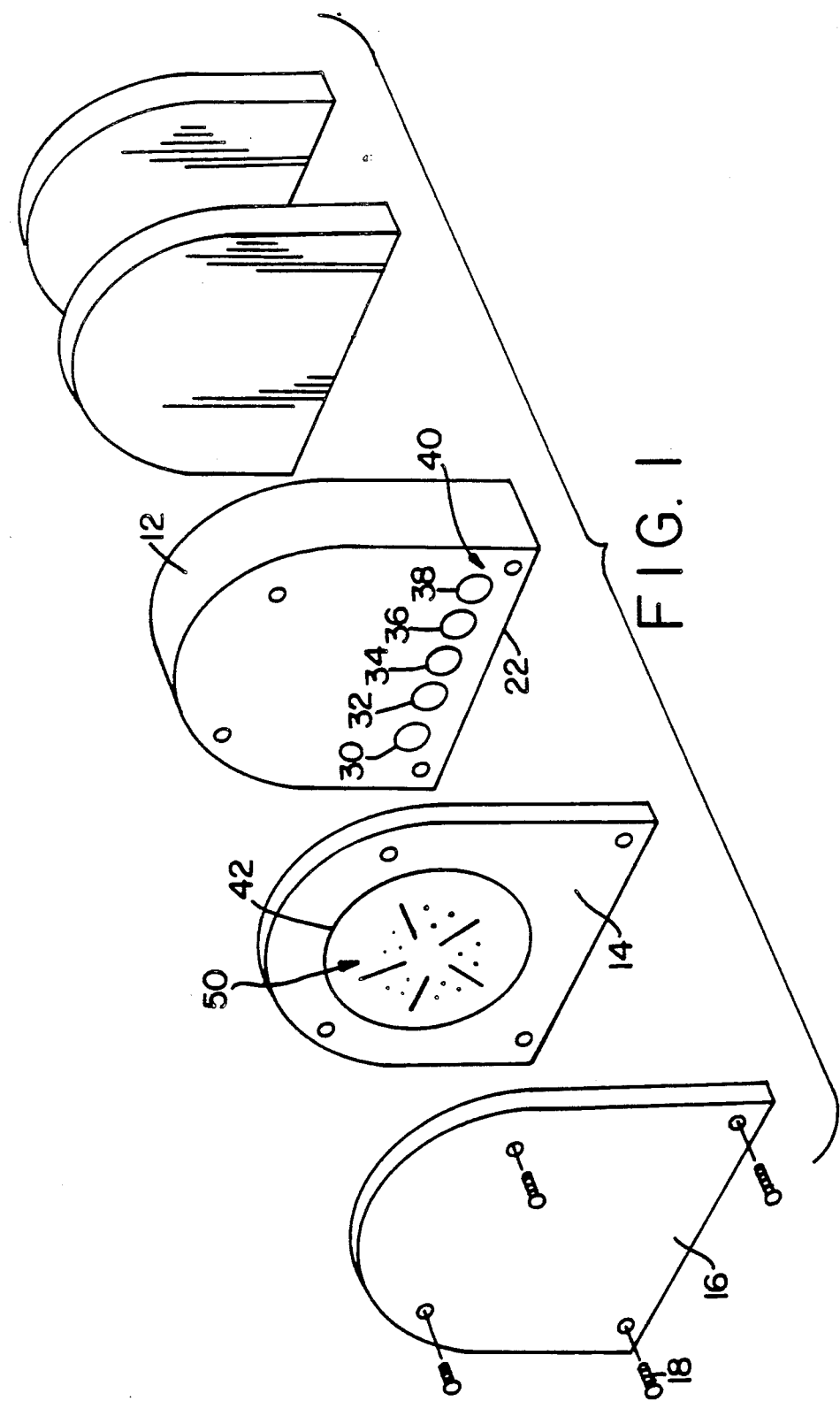

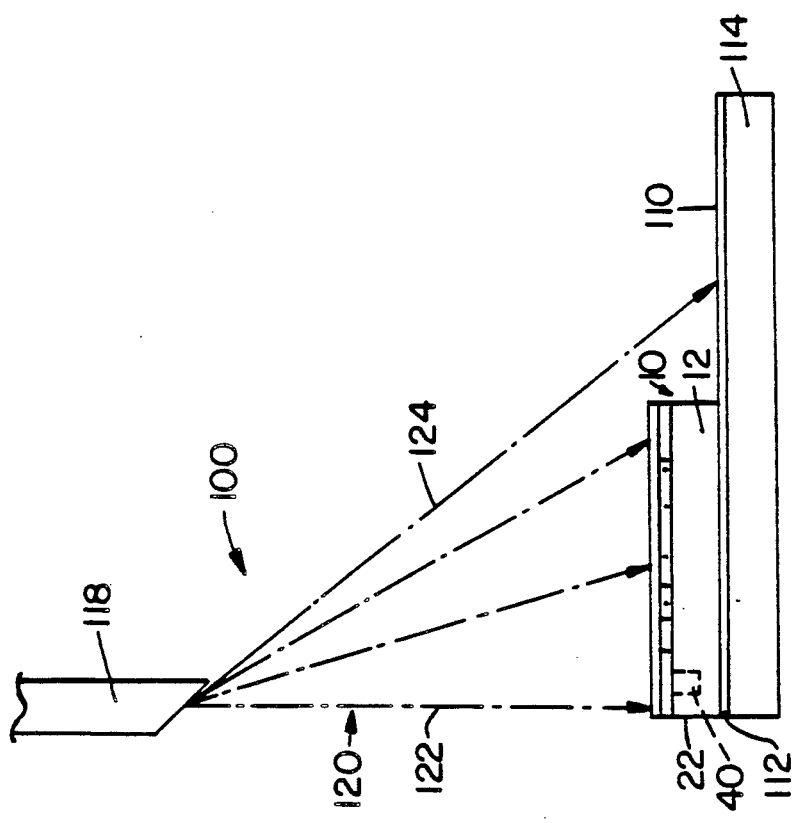
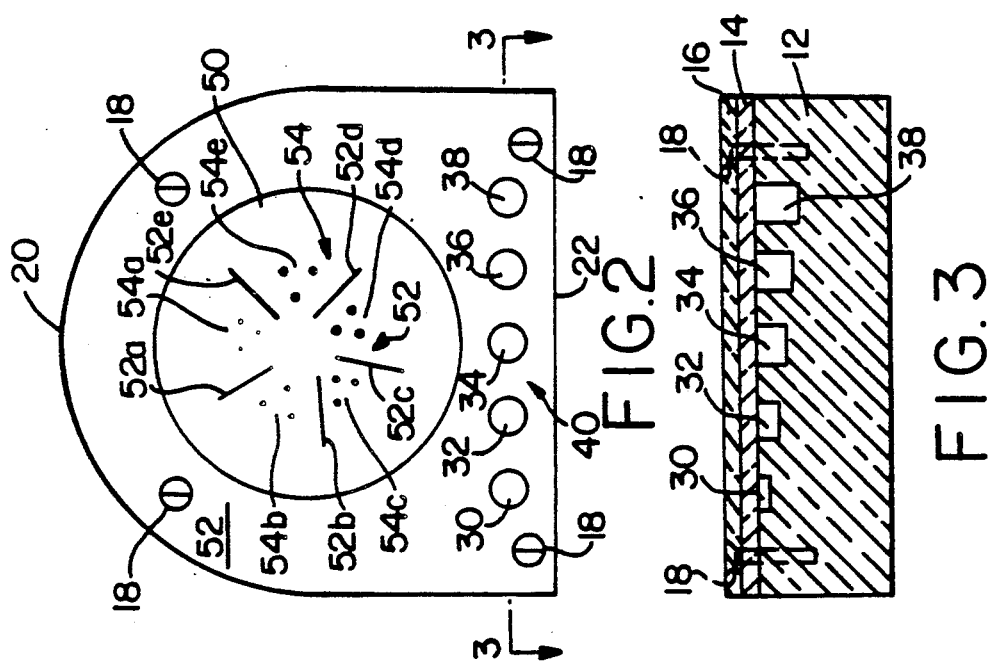

ORIENTED MAMMOGRAPHY PHANTOM

BACKGROUND OF THE INVENTION

The present invention relates to radiological phantoms, and in particular, to a radiological phantom for use in X-ray mammography.

Radiological mammographic examinations provide very early detection of the formation of cancerous deposits in the tissue of the breast. In order to perform such examinations, X-rays are passed through the breast tissue and expose an X-ray film. When developed, the film will contain an image of the tissue mass of the breast. Two mammographic indications of breast cancer, microcalcifications and soft tissue fibrillar extensions, are denser and more radiopaque than normal breast tissue and therefore, if present, will show up as light areas on the developed film. When detected early, these growths will be extremely small, as will the X-ray images they produce. Consequently, it is frequently difficult to discern the images produced by these growths from the image produced by the surrounding tissue. In order that the images of these small growths be reproduced clearly so as to be readily identifiable on the exposed film, it is essential that the radiologist know the overall performance and imaging capability of the radiological system so that it may be adjusted for peak performance.

An evaluation of the system is typically accomplished by exposing a stable test device, commonly referred to as a phantom, to the X-ray beam and examining the resultant image produced on the film. Generally, phantoms are designed to simulate the radiographic characteristics of a particular tissue mass. Thus, in the field of mammography, phantoms are particularly designed to provide a substantially equivalent attenuation of an X-ray beam as would breast tissue.

Mammographic phantoms typically include a resolution section and frequently include a step wedge section as well. The resolution section gauges the ability of the X-ray system to detect extremely small objects. Thus, the resolution section contains test objects of known size, frequently consisting of a plurality of small fibers and particles of varying sizes which are more opaque to X-rays than the surrounding phantom structure. These fibers and particles are designed to simulate microcalcifications and soft tissue fibrillar extensions which provide mammographic indications of breast cancer. Upon exposure of the phantom to an X-ray beam, the fibers and particles will produce images on the film; some fibers and particles will produce clearer images than others, while the smallest fibers and particles will not produce visible images at all. By determining the size of the smallest particle or fiber whose image is clearly produced on the film, the radiologist will know the limit of his system for detecting these warning signs of breast cancer.

The step wedge section consists of a series of regions having progressively increasing radiolucency which are used to determine the quality of the X-ray beam by gauging image contrast. Several mammography phantoms incorporate step wedges consisting of an array of holes, normally five (5), of varying depth. By comparing the optical densities of the circular images produced by the holes on both the reference film and test film, the beam quality can be evaluated. An example of a mammographic phantom having both the aforementioned resolution section and step wedge features is the Model No. 76-001 Mammographic QA Phantom produced by Nuclear Associates of Carle Place, N.Y.

Radiological systems for mammography basically consist of a flat horizontal support surface which defines the imaging plane of the system. As used herein, the term "imaging plane" refers to the region directly above the support surface where those objects whose images are to be reproduced on an X-ray film are positioned. Suspended above the support surface is an X-ray source from which X-ray beams are directed downwardly, through the object and support surface, to expose a film plate located in a holder beneath the support surface. During a mammographic examination, a breast would be positioned in the imagining plane so that the chest wall is adjacent one edge of the support surface. Thus, as the X-ray beams pass through the breast they create an image thereof on the film below. Similarly, when utilizing a phantom to evaluate the overall performance and imaging capability of the radiological system, the phantom is placed in the imagining plane so that upon exposure to the X-ray beam an image of the phantom will be created in the film.

With currently available mammography phantoms, such as the aforementioned phantom produced by Nuclear Associates, the radiologist must first examine the film in order to determine the orientation of the image before being able to identify which of the test objects were clearly reproduced.

Additionally, it is difficult to consistently locate currently available phantoms so that the step wedge is always in the same position relative to the X-ray beam. It is desirable to locate the phantom so that the step wedge is adjacent the center of the X-ray beam where the effects of beam scattering are minimized. As the position of the step wedge changes, the effect of beam scattering on the contrast measurements produced by the step wedge will vary, and hence the measurements will be less reliable.

Consequently, a need exists for a solution to these problems.

SUMMARY OF THE INVENTION

In accordance with the present invention, these needs have now been addressed by the invention of a radiographic phantom consisting of a generally planar, slab-like, at least partially radiolucent body having a non-uniform plan profile including a straight, edge, and having a series of regions of different radiolucency disposed adjacent the straight edge to cooperatively define a step wedge. The body further has at least one test object fixedly mounted thereto, the test object having a radiolucency less than the radiolucency of the body. Orienting means provided by the non-uniform plan profile orient the body in an imaging plane of a radiographic apparatus so that the plane of the body lies substantially in the imaging plane and the body lies in a predetermined orientation in the imaging plane, whereby each test object will lie substantially in a predetermined position in the imaging plane. The step wedge desirably lies in a predetermined location in the imaging plane adjacent the center of the X-ray beam so as to minimize the effects of beam scattering on the contrast measurements produced by the step wedge.

In accordance with one embodiment of the invention, the body preferably has an arcuate edge opposite the straight edge to provide the body with a generally D-shaped plan profile.

The at least one test object may include a plurality of test objects of differing sizes fixed to the body, whereby the test objects will lie in predetermined orientations relative to one another in the imaging plane when the body is oriented by the orienting means. Desirably, the test objects will consist of particles and fibers which simulate microcalcifications and soft tissue fibrillar extensions in breast tissue. These test objects are preferably fixed to the body in a plane parallel to the imaging plane, so that the test object plane is located a predetermined distance from a support surface when the generally planar body overlies the support surface of the imaging apparatus. Preferably, the predetermined distance is from about 2.8 cm to about 3.2 cm which simulates the region in the average compressed breast where the microcalcifications and soft tissue fibrillar extensions are normally found. Thus, by locating the test objects in a plane about 2.8 cm to about 3.2 cm from the support surface, the test objects will be in the focused region of the X-ray beam and the images they produce on the film will have a high degree of resolution.

In yet another embodiment, the phantom further includes at least one generally planar, slab-like, at least partially radiolucent plate, the plane of the plate being superposed upon the plane of the body in stackable arrangement.

Preferred embodiments of the present invention provide a radiographic phantom wherein the location of the particular test features can be repeatedly reproduced from one test to the next so that the image of each test feature may be readily located on an X-ray film. In addition, preferred embodiments of the present invention provide a radiographic phantom having a step wedge positioned to provide more accurate contrast measurements by reducing the effects of scattering of the X-ray beam.

Moreover, the preferred radiographic phantom according to the present invention has a simple structure which is easy to manufacture and use.

BRIEF DESCRIPTION OF THE DRAWING

A more complete appreciation of the subject matter of the present invention and the various advantages thereof can be realized by reference to the following detailed description, in which reference is made to the accompanying drawings in which:

FIG. 1 is an exploded perspective view showing the assembly of the elements of a radiographic phantom, including optional plates for increased attenuation, in accordance with one embodiment of the present invention;

FIG. 2 is a plan view of the radiographic phantom of FIG. 1; and

FIG. 3 is a cross-sectional view of the radiographic phantom taken along line 3—3 of FIG. 2, and not including the optional attenuation plates.

FIG. 4 is a schematic elevational view showing the use of the phantom of FIG. 1 in a radiological apparatus.

DETAILED DESCRIPTION

As shown in FIG. 1, radiographic phantom 10 has a generally planar, slab-like construction. By utilizing the terms "planar" and "slab-like", it is meant that the radiographic phantom 10 has a dimension in one plane which is substantially greater than its dimension in the direction perpendicular to that plane.

Radiographic phantom 10 includes a bottom plate 12, a spacer 14 and a cover plate 16 superposed with one another and held in assembled position, typically with screws as at 18. Base plate 12, spacer 14 and cover plate 16 are formed from a material which is at least partially translucent to X-rays, thereby allowing X-rays to pass therethrough without being totally deflected or attenuated. This property will hereinafter be referred to as radiolucency. Preferably, this radiolucent material will simulate the attenuation characteristics of the tissue being tested. In the case where breast tissue is to be analyzed, visibly transparent acrylic plastics produce an acceptable attenuation, although other materials which produce an appropriate attenuation may be used. The thicknesses of base plate 12, spacer 14 and cover plate 16 are chosen so that, when sandwiched together to form phantom 10, the attenuation produced by the sandwich is equivalent to the attenuation produced by an average sized breast. Preferably, when formed from visibly transparent acrylic plastic, phantom 10 will have a thickness of about 3.7 cm, corresponding to an approximately 4.5 cm compressed average breast. FIG. 2 shows an embodiment of phantom 10 as it would appear if formed from visibly transparent acrylic plastic.

As readily seen in FIGS. 1 and 2, bottom plate 12, spacer 14 and cover plate 16 all have a coextensive D-shaped plan profile. Thus, each of base plate 12, spacer 14 and cover plate 16 has an arcuate edge 20, the ends of which are connected by a straight edge 22.

Adjacent and parallel to straight edge 22, base plate 12 includes a linear array of blind holes 30, 32, 34, 36, and 38 which cooperatively define a step wedge generally indicated as 40. While the blind holes have substantially the same diameter, the depth of the holes progressively increases from the shallowest hole 30 at one end of the array to the deepest hole 38 at the opposite end of the array. As a result of their varying depth, each of the holes of step wedge 40 has a different radiolucency which gradually increases from the shallowest hole 30 to the deepest hole 38. The more radiolucent the hole, the darker the image of the hole will be in the exposed film. In order to provide meaningful contrast information, the depth of the holes typically range from about 0.10 inches to about 0.50 inches. Thus, the depth of hole 30 normally will be about 0.10 inches; the depth of hole 32 will be about 0.20 inches; the depth of hole 34 will be about 0.30 inches; the depth of hole 36 will be about 0.40 inches; and the depth of hole 38 will be about 0.50 inches.

Located in a region adjacent arcuate edge 20, spacer 14 includes a circular opening 42 which forms a resolution section generally indicated as 50. Resolution section 50 is filled with a waxy substance, such as paraffin wax, embedded with test objects which are designed to simulate the microcalcifications and soft tissue fibrillar extensions which are two mammographic indications of breast cancer. Thus, resolution section 50 includes both fibers, indicated generally at 52, and particles, indicated generally at 54, both the fibers 52 and particles 54 being more radiopaque than the surrounding waxy substance and remaining phantom structure so as to produce a discernable film image. Fibers 52 radiate outwardly from a central portion of resolution section 50, increasing in diameter in a counterclockwise direction. For example, fiber 52a may have a diameter of 0.20 mm; fiber 52b a diameter of 0.34 mm; fiber 52c a diameter of 0.43 mm; fiber 52d a diameter of 0.55 mm; and fiber 52e a diameter of 0.70 mm. The fibers 52 are formed from a material such as nylon or the like which will simulate soft tissue fibrillar extensions in breast tissue.

Particles 54 are located in the regions between the fibers 52. Each region includes several discrete particles of the same size, the particles in adjacent regions increasing in diameter in a counterclockwise direction. Thus, for example, particles 54a may have a diameter of 0.10 mm; particles 54b a diameter of 0.12 mm; particles 54c a diameter of 0.17 mm; particles 54d a diameter of 0.23 mm; and particles 54e a diameter of 0.275 mm. Each particle 54 is formed from a material which will simulate the microcalcifications which form as an early indication of cancer in breast tissue. Although calcium carbonate is the preferred material for forming particles 54, other like materials may also be used.

While the thickness of phantom 10 is designed to simulate the radiological attenuation corresponding to the tissue in an average sized compressed breast, plate 60 may optionally be used in conjunction with phantom 10 in order to simulate the radiological attenuation of compressed breast tissue which is larger than average. Thus, plate 60 is a generally slab-like planar structure having a perimeter which corresponds to the perimeter of phantom 10. Preferably, plate 60 is formed from the same acrylic material which forms phantom 10. In such case, a plate 60 having a thickness of about 0.8 cm will simulate approximately 1.0 cm of additional average compressed breast tissue. More than one plate 60 may be provided for those situations where greater amounts of attenuation are desired.

FIG. 4 shows the use of the phantom 10 to evaluate a radiological apparatus, generally indicated as 100, in accordance with the present invention. Apparatus 100 is a conventional imaging apparatus of the type used for mammography, and includes a flat, horizontal support surface 110 having a fixed reference 112 at one edge thereof. Reference 112 may be a separate structural element located at the edge of horizontal support surface 110 or may simply be the straight edge of the support surface 110 itself. Located beneath surface 110 is a cartridge assembly 114 which houses X-ray film in a plane essentially parallel to the support surface 110. Suspended above the support surface 110 is an X-ray source 118 which directs an X-ray beam 120 toward the support surface 110 and the film therebelow. As can be seen in FIG. 4, X-ray beam 120 is configured to have a central portion 122 incident upon the film at an angle of about 90° to the plane of the film adjacent reference 112 of the support surface, and an outer or heel portion 124 incident upon the film at an angle somewhat less than 90°. In order to gain the benefit of the positioning of the step wedge 40 on phantom 10, the phantom is oriented in the imaging plane above the support surface so that straight edge 22 is positioned in alignment with fixed reference 112. By positioning the phantom 10 in such a manner, step wedge 40 may consistently be located adjacent the center portion 122 of the X-ray beam where the effects of beam scattering are minimized. Also, each particle 54 and each fiber 52 is positioned at a predetermined location with respect to reference 112 of the imaging apparatus. As resolution section 50 is remote from the straight edge 22 of the phantom body, the resolution section, and hence the particles 54 and fibers 52, will always be disposed in the heel portion 124 of the X-ray beam. The smallest particles 54a and smallest fiber 52a will always be disposed furthest from reference 112, in a region where the X-ray beam intersects the film at a low angle of incidence.

In addition, phantom 10 is placed in the imaging plane so that base plate 12 is adjacent support surface 110, with any plates 60 which may be used inserted between the base plate and the support surface. This orientation locates the test objects in a plane about 2.8 cm to about 3.2 cm from the support surface which simulates the location in which microcalcifications and soft tissue fibrillar extensions are normally found in an average compressed breast, and which therefore is the focused region of the X-ray beam.

The exposure of phantom 10 to the X-ray beam 120 will create an image of certain fibers 52 and particles 54, as well as the step wedge 40, on the film. By comparing the contrast of the step wedge image reproduced in the test film with the image contrast in a reference film, the radiologist can determine the quality of the X-ray beam. Poor image contrast may be associated with equipment problems, for example, an inferior X-ray beam, signaling to the radiologist that adjustments or repairs are needed.

Once it has been determined that the X-ray beam is of adequate quality, the image produced by the resolution section 50 may then be examined to identify the smallest fiber 52 and particle 54 which may be discerned from the background of the film. As phantom 10 has a straight edge 22 which permits the consistent placement of the phantom in the imaging plane of an X-ray beam, the image of the fibers 52 and particles 54 will always have the same orientation on the film. Thus, in reading the film produced by phantom 10, the radiologist will always look in the same location on the film for the various fibers 52 and particles 54, and thus the size of the smallest fiber 52 and particle 54 clearly reproduced on the film is readily determined. Because each particle 54 and each fiber 52 is located in the same portion of the beam on every test, each particle and each fiber is exposed at the same beam incidence angle on every test. Therefore, the test gives repeatable results. Because the smallest particles and fibers are exposed at a relatively low incidence angle, the test simulates a "worst-case" condition in a real mammographic examination, wherein a small calcification or a small fibrillar extension occurs in a region of the breast falling in the heel region of the beam.

Although the invention herein has been described with reference to particular embodiments, it is to be understood that these embodiments are merely illustrative of the principals and applications of the present invention. It is therefore to be understood that numerous modifications may be made to the illustrative embodiments and that other arrangements may be devised without departing from the spirit and scope of the present invention as defined by the appended claims.

I claim:

1. A radiographic phantom comprising,
    (a) a generally planar, slab-like at least partially radiolucent body having a non-uniform plan profile including a straight edge,
    (b) a series of regions of differing radiolucency disposed on said body adjacent said straight edge and cooperatively defining a step wedge,
    (c) a plurality of test objects including particles and fibers of differing sizes fixedly mounted to said body and having a radiolucency less than the radiolucency of said body, and
    (d) orienting means provided by said non-uniform plan profile to orient said body in an imaging plane of a radiographic apparatus so that the plane of said body lies substantially in said imaging plane and said body lies in a predetermined orientation in said imaging plane, whereby said test objects will lie in predetermined orientations relative to one another in said imaging plane when said body is oriented by said orienting means.

2. A phantom as claimed in claim 1 wherein said fibers have a diameter from about 0.10 mm to about 0.80 mm.

3. A phantom as claimed in claim 1 wherein said particles have a diameter from about 0.05 mm to about 0.35 mm.

4. A phantom as claimed in claim 1 wherein said particles simulate microcalcifications in breast tissue.

5. A radiological phantom as claimed in claim 4 wherein said particles are formed from calcium carbonate.

6. A phantom as claimed in claim 1 wherein said fibers simulate soft tissue fibrillar extensions in breast tissue.

7. A phantom as claimed in claim 6 wherein said fibers are formed from nylon.

* * * * *